United States Patent [19]

Long

[11] Patent Number: 4,884,345

[45] Date of Patent: Dec. 5, 1989

[54] ADJUSTABLE TEMPLATE FOR PACEMAKER ECG ANALYSIS AND METHOD OF USE

[75] Inventor: Ronald J. Long, Simi Valley, Calif.

[73] Assignee: Siemens-Pacesetter, Inc., Sylmar, Calif.

[21] Appl. No.: 193,329

[22] Filed: May 12, 1988

[51] Int. Cl.[4] .................. A61N 1/00; H05G 00/00; A61B 5/04; G01B 3/02

[52] U.S. Cl. ...................................... 33/1 C; 128/710; 128/702; 128/419 P

[58] Field of Search ............... 128/702, 703, 704, 708, 128/710, 419 P; 33/1 C, 1 B, 562, 563; 235/70 A, 40 B

[56] References Cited

U.S. PATENT DOCUMENTS

| | | | |
|---|---|---|---|
| 2,088,533 | 7/1937 | Phelps | 128/710 |
| 2,501,550 | 3/1950 | Tamagua et al. | 33/1 C |
| 3,287,814 | 11/1966 | Littmann | 128/710 |
| 3,940,692 | 2/1976 | Neilson | 128/702 |
| 4,023,276 | 5/1977 | Furukawa et al. | 33/1 C |
| 4,030,486 | 6/1977 | Eastman | 33/1 C |
| 4,550,502 | 11/1985 | Grayzel | 128/702 |

OTHER PUBLICATIONS

Patent Application: Ser. No. 06/670,474; filed 11/09/84; Caliper Device for Measuring Time Intervals on a Dual—Chamber Pacemaker Electrocardiogram (Long).

*Primary Examiner*—Francis J. Jaworski
*Assistant Examiner*—George Manuel
*Attorney, Agent, or Firm*—Bryant R. Gold; Leslie S. Miller; Lisa P. Weinberg

[57] ABSTRACT

An adjustable template device for pacemaker ECG analysis is similar to a slide rule with a transparent window portion which can be laid over an ECG trace to aid in its analysis. A frame for the template has a back member and a cover member connected together with rivets, with the cover member having cutout portions through which various scales printed on the back portion can be seen. A series of movable transparent plastic sheets slide back and forth independently in the frame to allow measurement of time intervals on the ECG trace. Fiducial marks on the movable sheets indicate time intervals by their positions with respect to scales on the back member. AV, AE, MT, PVAR, and pacing intervals can all be set simultaneously on the template. A photocopy of the template overlying the ECG trace can be made to provide a permanent record.

11 Claims, 6 Drawing Sheets

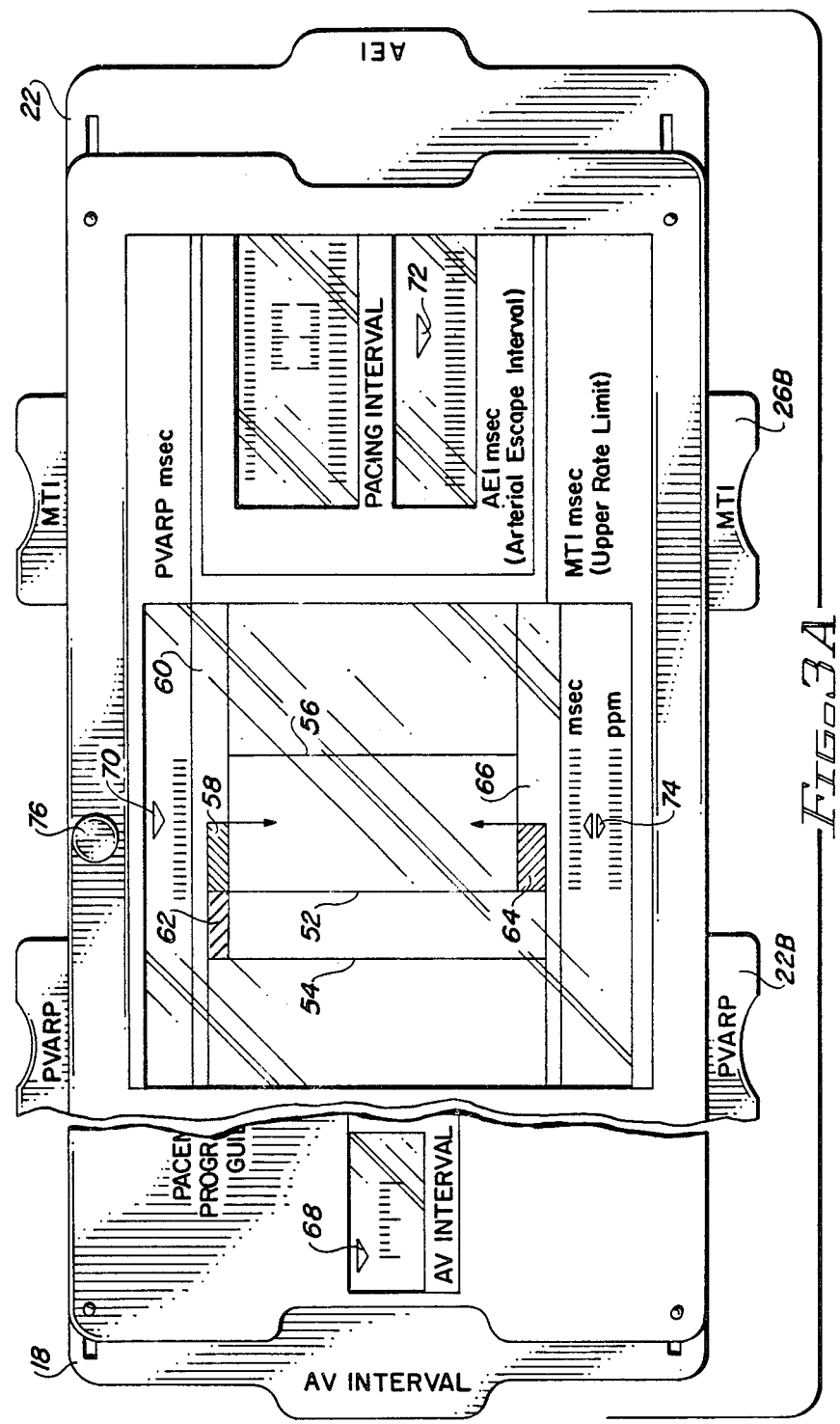

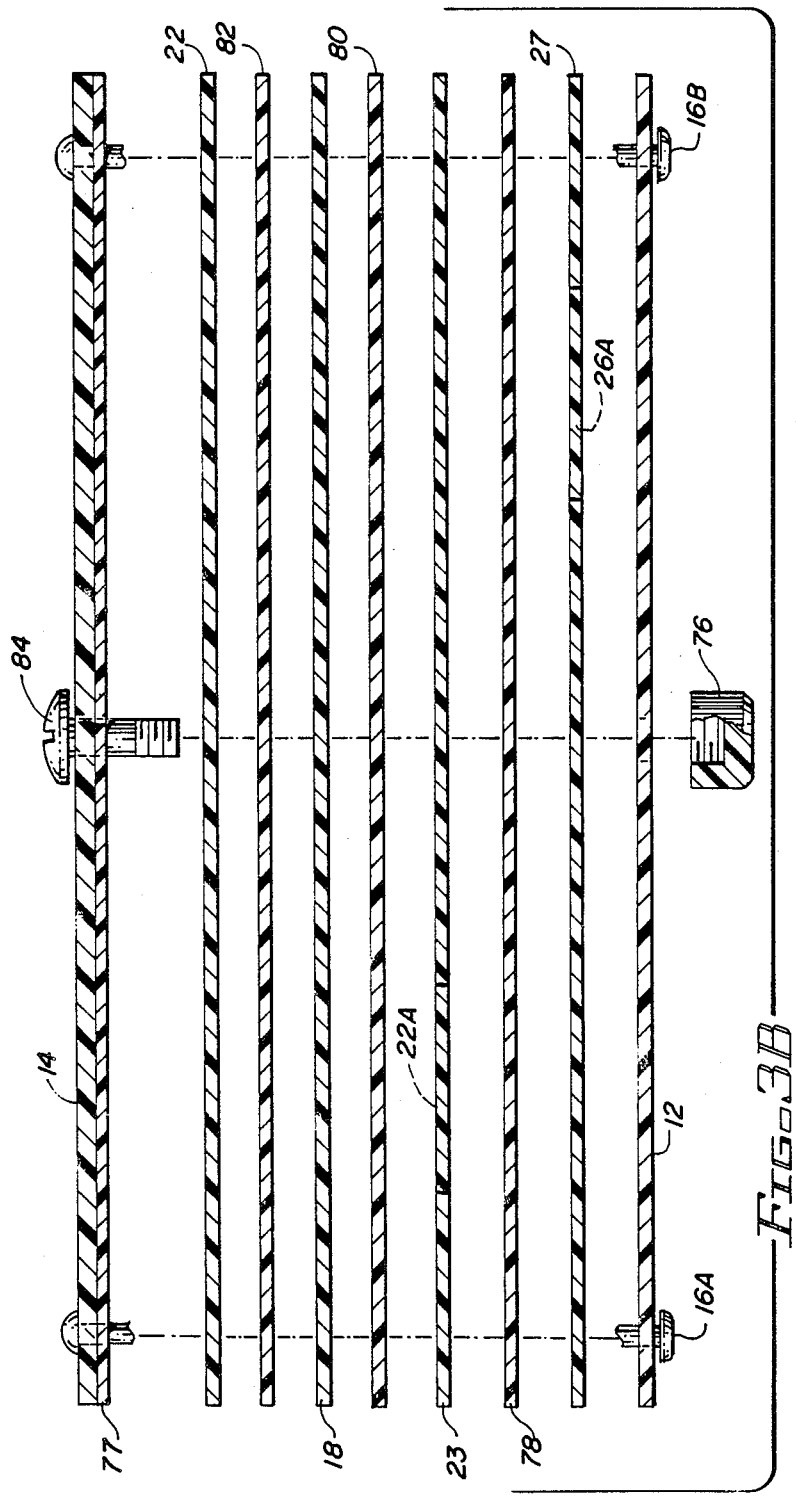

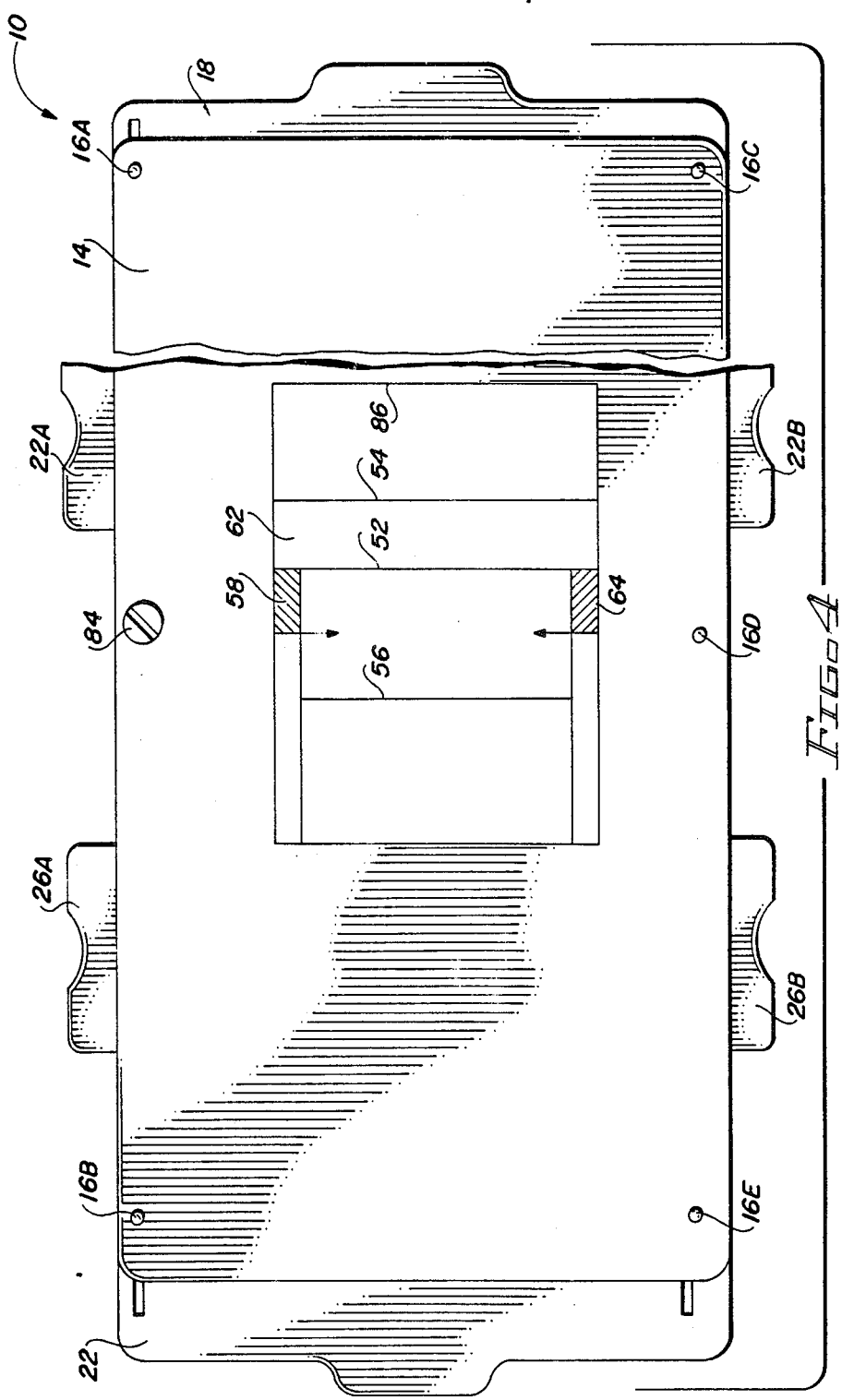

ADJUSTABLE TEMPLATE FOR PACEMAKER ECG ANALYSIS AND METHOD OF USE

This invention relates to devices for aiding in the analysis of pacemaker ECG traces and, more particularly, to an adjustable template device and a method for using it as such an aid.

BACKGROUND OF THE INVENTION

An electrocardiogram, or ECG, is an important aid in the diagnosis of heart condition. It is a graphic tracing of the electric current generated by the heart muscle during a heartbeat. The tracing is recorded with an electrocardiograph (historically a relatively simple string galvanometer), and it provides information on the condition and performance of the heart. Electrocardiograms are made by applying electrodes to various parts of the body to lead off the miniscule heart current to the recording instrument. The four extremities and the chest wall have become standard sites for applying the electrodes. After the electrodes are in place and conductive contacts are assured through the application of a salt paste, the instrument may be calibrated by the application of a standard voltage from a source outside the body. Standardizing electrocardiograms makes it possible to compare them as taken from person to person and from time to time from the same person.

The normal electrocardiogram shows typical upward and downward deflections that reflect the alternate contraction of the atria (the two upper chambers) and of the ventricles (the two lower chambers) of the heart. The first upward deflection, P, is due to atrial contraction or depolarization of the atria and is known as the atrial complex. The other deflections, Q, R, S and T, are all due to the action of the ventricles and are known as the ventricle complexes. The QRS wave (sometimes referred to as an R-wave, the predominant wave of the group), represents the depolarization of the ventricles, while the T-wave represents the repolarization of the ventricles. (It is noted that the atria also are repolarized, but this atrial repolarization occurs at approximately the same time as the depolarization of the ventricles; and any electrical signal generated by atrial repolarization is generally minute and is masked out by the much larger QRS-wave on the electrocardiogram.)

Any deviation from the norm in a particular electrocardiogram is indicative of a possible heart disorder. Information that can be obtained from an electrocardiogram includes whether the heart is enlarged and where the enlargement occurs, whether the heart action is irregular and where the irregularity originates, whether a coronary vessel is occluded and where the occlusion is located, and whether a slow rate is physiological or caused by heart block. The presence of high blood pressure, thyroid disease, and certain types of malnutrition may also be revealed by an electrocardiogram.

The technology of cardiac pacemakers has developed to a high level of sophistication of system performance. The current generation of cardiac pacemakers incorporates microprocessors and related circuitry to sense and stimulate heart activity under a variety of physiological conditions. These pacemakers may be programmed to control the heart in correcting or compensating for various heart abnormalities which may be encountered in individual patients.

The interpretation of electrocardiograms is not a simple task. It generally requires specialized training and even then opinions may differ regarding the interpretation of particular configurations of heart signal waveforms and concomitant symptom. In some cases certain symptoms may be overlooked as, for example, when the corresponding signal waveform aberration occurs only rarely on an intermittent basis.

The use of a pacemaker in stimulating heart activity generally complicates the task of interpreting corresponding electrocardiograms. The stimulating pulses tend to induce a certain artificiality to the heart signal waveform with a resultant electrocardiogram that is even more difficult to interpret if the pacing pulses are sometimes present and then occasionally inhibited because of intermittent normal heart activity.

In order to efficiently perform its function as a pump, the heart must maintain a natural AV synchrony. The term "AV synchrony" relates to the sequential timing relationship that exists between the contractions of the atria and the ventricles. The P-QRS-T cycle of waves represents the natural AV synchrony of the heart. These waves, including the time relationships that exist therebetween, are carefully studied and monitored through conventional ECG techniques whenever the operation of the heart is being examined.

An electrocardiogram is the primary tool for checking on the functioning of a pacemaker after it has been implanted. The record can be made in real time and, as noted, commonly consists of a tracking on a strip chart recorder. The strip chart usually consists of graph paper on which the smallest division is one millimeter, with every fifth line being accented to outline larger squares which are five millimeters on a side. The continuous strip of graph paper is moved beneath the recording pen at such a rate that each millimeter square corresponds to 40 milliseconds (ms), and each larger square corresponds to a time period of 200 ms.

It is common practice for a cardiologist to analyze an ECG from a patient using a pair of calipers or dividers. Using dividers, a cardiologist can measure a time interval between any two events occurring on the ECG trace. For example, to determine the pacing rate of a patient's single-chamber pacemaker, the cardiologist measures the distance between any two consecutive pacing stimuli. To accomplish this, the points of the divider are placed on the ECG trace between two consecutive pacing stimuli and then, with the divider spacing set, the pointers are placed on the ECG strip starting at some fixed reference line to measure the pacing period. Since there are 60,000 ms in one minute, dividing the pacing period in ms into 60,000 yields the rate in beats per minute. Also, the dividers set to the pacing period may be placed elsewhere on the ECG trace to compare subsequent intervals of similar pacing stimuli.

In determining the pacing rate from an ECG trace for a dual-chamber cardiac pacemaker, measurement of two intervals is required, namely the time from an atrial stimulus to a ventricular stimulus (AV interval) plus the time from the ventricular stimulus to the next atrial stimulus (VA′ or atrial escape interval). Using a standard pair of dividers, a cardiologist must reset the dividers between measuring the AV and VA intervals and must again and again reset the dividers when comparing such intervals with similar subsequent intervals. Such operations are time consuming and subject to inaccuracies.

One particular caliper-type device, which has been marketed, is known in the prior art as a Trivider caliper. This caliper comprises a divider having three legs which allow simultaneous measurement of time intervals between any three events occurring on an ECG trace (e.g., AV and VA) without resetting or adjusting the caliper.

It would be a great boon to the art of analyzing pacemaker ECG traces if there were a device that allowed the measurement of more than two intervals at one time. If such a device were lightweight, compact, and lacked the sharp points associated with calipers, it would be easier to carry in one's pocket and would be safer and more convenient to use.

SUMMARY OF THE INVENTION

The present invention provides an adjustable template for pacemaker ECG analysis which has the desirable features listed above. The adjustable template comprises a device similar to a slide rule, but has a transparent window portion which can be laid over an ECG trace to aid in its analysis. A frame for the template has a back member and a cover member connected together with rivets, with the cover member having cutout portions through which various scales printed on the back portion can be seen. A series of transparent plastic sheets can slide back and forth independently between the back and cover members to allow measurement or marking of time intervals on the ECG trace over which the template is laid. Tabs projecting from each of the sheets provide convenient means for manipulating them. The various sheets have slotted portions which accommodate the frame rivets as the sheets are moved with respect to the frame.

A base reference line on the back cover provides a zero time reference. An AV interval sheet and an AEI sheet with fiducial lines at their right and left extremities, respectively, can be moved left and right, respectively, to measure AV and AE intervals on the ECG tracing. Indicator arrows on the AVI and AEI sheets are used to read time intervals on AVI and AEI scales, respectively, on the back member. An AV interval scale printed on the AEI sheet moves between a pulses-per-minute scale and a pacing-interval scale printed on the back portion. A maximum tracking interval (MTI) sheet has an opaque portion which can be moved to the right of the base reference line to uncover a first transparent colored portion immediately above an MTI scale, and a postventricular atrial refractory period (PVARP) sheet has a similar opaque portion immediately below a PVARP scale which can be moved to uncover a second transparent colored portion to denote a PVARP interval. Stationary divider sheets separate the MTI, PVARP, AVI, and AEI sheets.

All time intervals can be measured simultaneously, so that the adjustable template of the present invention is a marked improvement over previous devices for pacemaker ECG analysis. In addition, the template and ECG trace can be photocopied to provide a permanent record of the measurements made.

BRIEF DESCRIPTION OF THE DRAWINGS

The above and other objects, features, and advantages of the present invention will be more apparent from the following more particular description thereof presented in conjunction with the accompanying drawings, wherein:

FIG. 3A is a front plan view of the adjustable template with all four sheets moved partway through their respective ranges of motion;

FIG. 3B is a top view of the adjustable template as adjusted in FIG. 2; and

FIG. 4 is a back plan view of the adjustable template as adjusted in FIG. 3A.

DETAILED DESCRIPTION OF THE INVENTION

The following description is of the best presently contemplated mode of carrying out the invention. This description is not to be taken in a limiting sense but is made merely for the purpose of describing the general principles of the invention. The scope of the invention should be determined with reference to the attached claims.

Figure 1A:
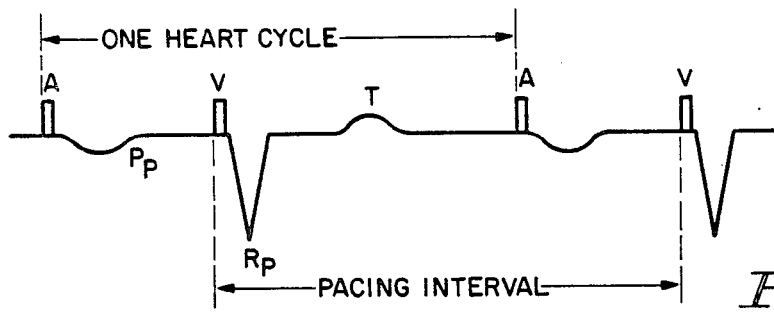
FIGS. 1A-1D are timing diagrams which show some possible sequences of cardiac events and define various time intervals that are used in the operation of a dual-chamber demand-type pacemaker.

Before describing the present invention in detail, it will be instructive to briefly review some of the timing intervals that are important in pacemaker operation. FIG. 1A shows a timing diagram that illustrates the response of the heart to stimulation pulses that are generated by an implanted pacemaker. In response to an atrium stimulation pulse, or A-pulse, delivered to the right atrium by the pacemaker lead, both atria contact and a P-wave is generated. Because the stimulating A-pulse originates from a different point within the right atrium than does the normal stimulating pulse from the sino-atrial node, the P-wave generated in response to this A-pulse does not appear the same as a naturally occurring P-wave. It is referred to as a $P_p$-wave, indicating that it is a paced P-wave, or a P-wave in response to a pacing signal. Similarly, in response to a stimulation pulse applied to the right ventricle, an R-wave is generated, represented in FIG. 1A as an inverted $R_p$-pulse. The R-wave in FIG. 1A is shown inverted because the stimulating pulse propagates through the ventricle chamber in a different direction than does the natural stimulating pulse that propagates through the left and right bundle branches. For purposes of this application, the natural responses or natural depolarizations of the heart are represented as a positive P-wave (a waveform going in the upwards direction) and a positive R-wave. Depolarizations of the atria or ventricles in response to an externally generated stimulation pulse such as occurs with a pacemaker are represented as a negative going $P_p$ or $R_p$-wave.

Figure 1B:
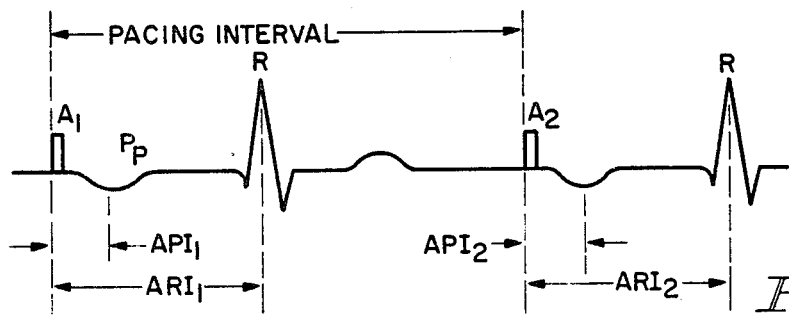

With reference to FIG. 1B, one possible response to atrium stimulation pulses, A, is shown. As is seen in FIG. 1B, in response to the pulse $A_1$, a $P_p$-waveform is generated a short time later, which time interval is identified as $API_1$ (referring to the first A-P interval). In response to the atria depolarization evidenced by the $P_p$-wave, and in the absence of A-V block, the ventricles depolarize and contract without the need of a stimulation pulse. Such depolarization occurs at a time $ARI_1$ later (referring to the first A-R interval of the sequence shown in FIG. 1B). At an appropriate time subsequent to the generation of the first atrium stimulation pulse $A_1$, a second atrium stimulation pulse, $A_2$ is generated by the pacemaker. In response to the $A_2$ stimulus, a second $P_p$-wave is generated at time $API_2$ after the generation of the $A_2$ pulse. Again, a naturally occurring R-wave occurs at a time $ARI_2$ subsequent to the generation of the $A_2$.

Figure 1C:
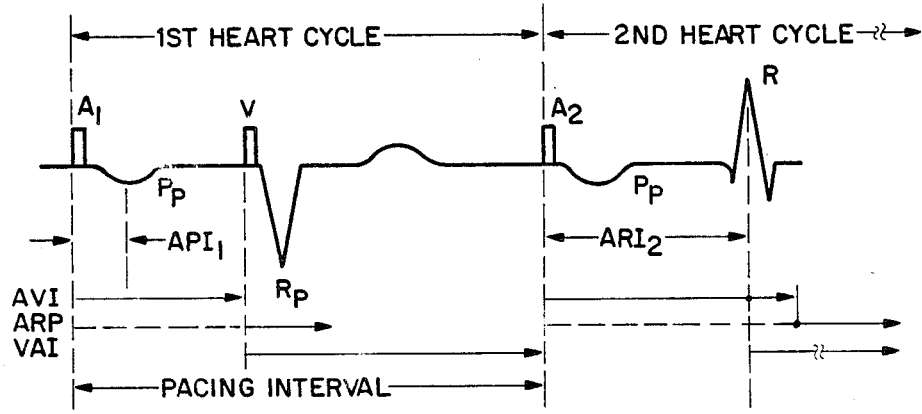
Figure 1D:
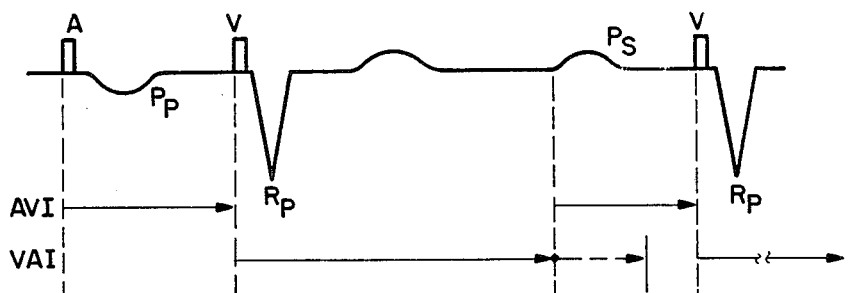

Referring next to FIGS. 1C and 1D, there are shown further timing diagram that define various intervals that are commonly used in controlling a dual-chamber demand-type pacemaker. In a demand-type pacemaker it is common to define an escape interval as a time period during which activity within the heart is sensed. If a natural cardiac event occurs during this escape interval, that is, if a natural P-wave or R-wave is sensed, then a corresponding stimulating pulse need not be generated. Not only does this mode of operation allow the heart to function in its natural state, if it is able to, but it also helps to conserve the limited energy stored within the battery of the pacemaker. In FIG. 1C it is seen that both the A-P interval and the A-R interval are illustrated as in FIG. 1B. Also shown in FIG. 1C, however, is an AVI, or A-V interval. This is a prescribed time set by the pacemaker during which a naturally occurring R pulse must occur, if one is to occur, prior to the generation of a ventricle stimulation pulse, V. As indicated in FIG. 1C, the A-V interval has been completed for the first heart cycle shown, thereby causing the V-pulse to be generated. During the second heart cycle, however, the A-V interval has not yet been completed at the time when the naturally occurring R-wave appears. There is thus no need for the pacemaker to generate a V stimulation pulse during the second heart cycle. Also illustrated in FIG. 1C is an atrial refractory period, or ARP. During this refractory period, the normal sensing mechanisms used within the pacemaker are non-responsive. This refractory period is analogous to the natural refractory period of myocardial tissue immediately following depolarization, and prevents the pacemaker from detecting any depolarization signals or noise that might result in timing errors. The refractory period is made up of two components, the absolute refractory period (indicated by the dashed line), during which detection of all signals is blocked, and a noise sampling or relative refractory period (represented by the solid line) during which detected signals are evaluated for a repetitive rate. As will be evident from the discussion that follows, the atrial refractory period, or ARP, does not prevent the detection of a $P_p$-pulse because this pulse is detected using a sensing means different from the normal atrial sensing probe.

Also shown in FIG. 1C is a V-A interval, or VAI. The beginning of this interval is initiated by the generation of a V-stimulation pulse, or the sensing of a natural R-wave. This V-A interval, less the ARP, defines the time during which a natural (non-paced) P-wave must be detected if the A-stimulation pulse is to be inhibited. As is evident from FIG. 1C, the pacing interval or rate set by the pacemaker is equal to the V-A interval, VAI, plus the A-V interval, AVI. Hence, by varying or adjusting these two time periods, the pacing interval of the pacemaker can be controlled, thereby controlling the heart rate.

Referring next to FIG. 1D, a different cardiac event sequence is illustrated. In FIG. 1D it is seen that an A-pulse, or atrial stimulus, is first generated, causing $P_p$-wave (or atrial depolarization) to occur. The A-V interval is initiated by the generation of the A-pulse. At the conclusion of the A-V interval, a V-pulse or ventricle stimulation pulse is generated because no natural R-wave was sensed prior to that time. In response to the generation of the V-pulse the ventricle depolarizes as evidenced by the $R_p$-wave, and the next V-A interval is initiated. Before the V-A interval, or VAI, terminates, however, a natural P-wave (identified as P, and sometimes referred to as a sinus P-wave) occurs. Accordingly, there is no need for the pacemaker to generate an atrium stimulation pulse. The sensing of the P-wave re-initiates the A-V interval. During this interval, the sensors in the ventricle are monitoring the ventricle activity to determine if a naturally occurring R-wave is present. For the situation shown in FIG. 1D, a naturally occurring R-wave does not occur prior to the termination of the AVI, so a V pulse is generated, thereby causing a paced $R_p$-wave to occur, indicating ventricular contraction. It is to be understood that FIGS. 1C and 1D represent simplified timing diagrams of only two of a very large number of heart event sequences that can occur. FIGS. 1A–1D are presented merely to illustrate various timing intervals that a cardiac practitioner might be interested in when interpreting an ECG tracing.

Figure 2:
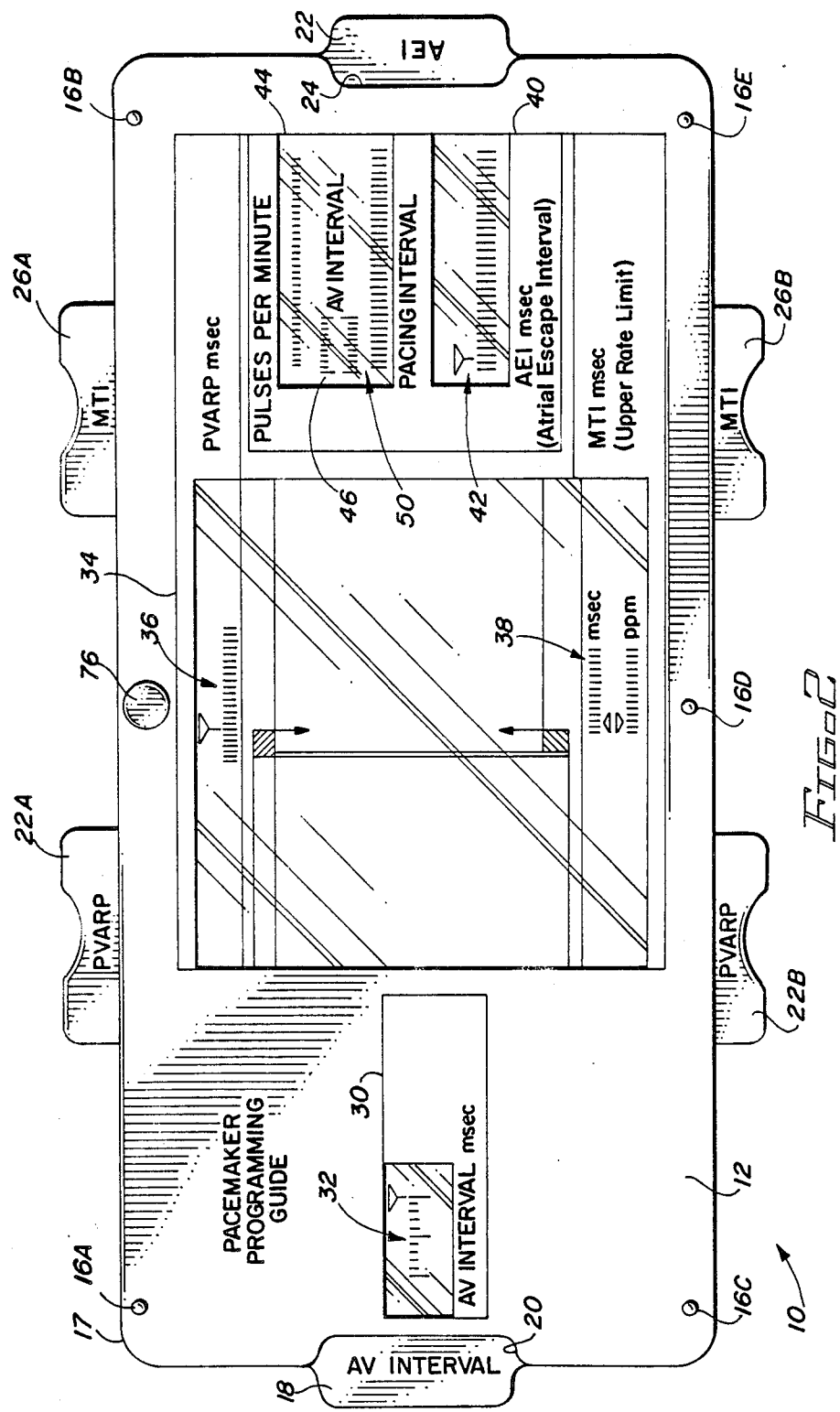
FIG. 2 is a plan view of the adjustable template of the present invention will all sheets retracted into the frame.
Figure 2A:
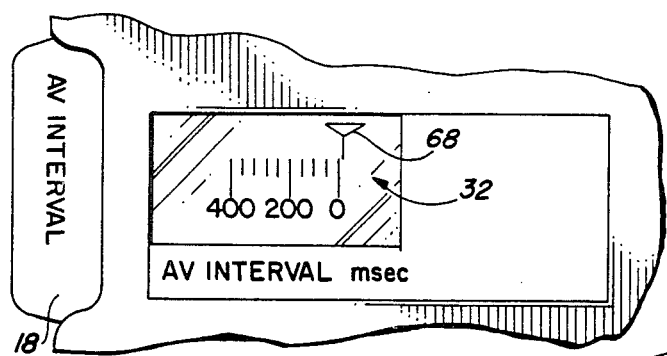
FIG. 2A is an enlarged view of the AV Interval (AEI) scale.
Figure 2B:
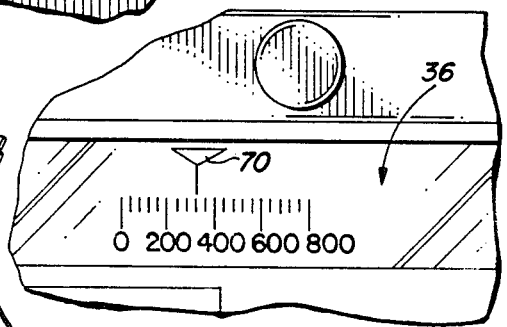
FIG. 2B is an enlarged view of the Post Ventricular Atrial Refractory Period (PVARP) scale.

An adjustable template for pacemaker ECG analysis in accordance with the present invention is shown in FIG. 2. In the front plan view shown in FIG. 2, 2a, 2b, 2c, and 2d adjustable template 10 comprises a cover member 12 connected to a back member 14 (FIG. 3B) by rivets 16a–16e. The combination of cover member 12, back member 14, and rivets 16a–16e constitutes a frame 17 which contains a series of movable sheets slidingly engaged therewithin. The various separate sheets can be distinguished in FIG. 2 by tabs which form part of the sheets and permit easy manipulation of the sheets. Thus, part of an AVI sheet 18 can be seen through a cutout portion 20 of cover member 12 and a part of an AEI sheet 22 can be seen through a cutout portion 24 of cover member 12.

Figure 2C:
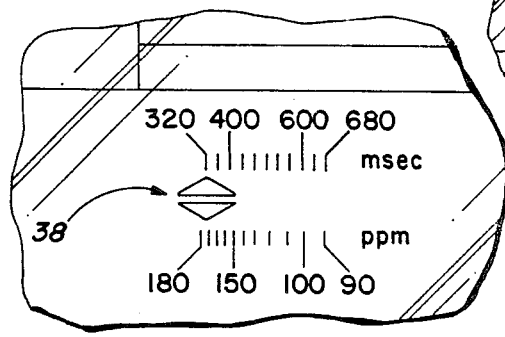
FIG. 2C is an enlarged view of the Maximum Tracking Interval (MTI) scale.
Figure 2D:
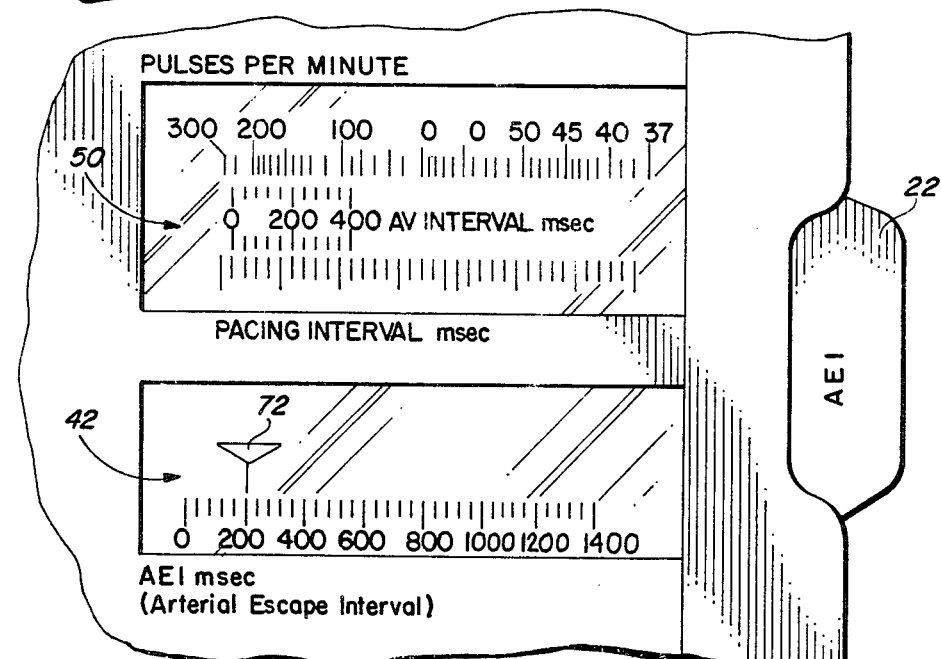
FIG. 2D is an enlarged view of the Atrial Escape Interval (AEI) and the Pacing Interval scale.

Projecting PVARP tabs 22a and 22b form part of PVARP sheet 23, and projecting tabs 26a and 26b form part of an MTI sheet 27. Various scales and markings on back member 14 can be seen through cutout portions of cover member 12. An AVI cutout portion 30 reveals an AV interval scale 32 (FIG. 2A), and a central cutout portion 34 in cover member 12 reveals a PVARP scale 36 (FIG. 2B) and an MTI scale 38 (FIG. 2C). An AEI cutout portion 40 reveals AEI scale 42 (FIG. 2D). Scales 30, 36, 38, and 40 are all imprinted on back member 14. A pacing interval cutout portion 44 reveals an A-V interval scale 46 which is printed on transparent AEI sheet 22, through which can be seen a pulses-per-minute scale 48 and a pacing interval scale 50 (FIG. 2D), both of which are printed on back cover member 14.

FIG. 3A shows adjustable template 10 with AVI sheet 18 and PVARP sheet 23 moved left with respect to frame 17, and with AEI sheet 22 and MTI sheet 27 moved right with respect to frame 17. The movement of a particular sheet is effected by holding frame 17 in one hand and grasping an available part of the sheet with the other hand to move it with respect to frame 17. For example, MTI sheet 27 is moved by moving either of the tabs 26a or 26b with respect to frame 17.

A base reference line 52 is printed on back member 14 to provide a zero reference time. AV fiducial line 54 and AEI fiducial line 56 are printed on transparent sheet members 18 and 22, respectively. Back member 14 has a transparent portion which coincides with central cutout portion 34 in cover member 12, so that an ECG tracing placed beneath adjustable template 10 can be seen. A first transparent colored portion 58 of back member 14 is situated directly below MTI scale 36, and an opaque portion 60 of PVARP sheet 23 obscures more or less of transparent colored portion 58 depending on the position of PVARP sheet 23. Immediately to the left of first transparent colored portion 58 is a cross-hatched colored portion 62 which is uncovered as AVI sheet 18 is moved from its rightmost position with respect to frame 17.

A second transparent colored portion 64 forming part of back member 14 is situated immediately above MTI scale 38, with an opaque colored portion 66 of MTI sheet 27 uncovering an amount of second transparent portion 64 proportional to the movement of MTI sheet 27 with respect to frame 17. Indicator arrow marks 68, 70, 72, and 74 serve to indicate the positions of the sheets on which they are printed with respect to the scales to which they are adjacent. Thus, MTI indicator arrow mark 74 as shown in FIG. 3A indicates a maximum tracking interval of 400 ms.

The positions of the various sheet members can be locked with respect to frame 17 by tightening knob 76 of locking means 84, shown more fully in FIG. 3B. FIG. 3B is a top view of adjustable template 10 for pacemaker ECG analysis. Frame 17 consists of cover member 12 and back member 14 connected by rivets 16a–16e (only 16a and 16b are visible in FIG. 3B). The side of back member 14 closest to cover member 12 is covered by transparent back sheet 77, which allows an ECG tracing to be seen through cutout portions of cover member 12 and back member 14. MTI sheet 27 is separated from PVARP sheet 23 by first divider sheet 78. PVARP sheet 23 is separated from AVI sheet 18 by second divider sheet 80. AVI sheet 18 is separated from AEI sheet 22 by third divider sheet 82. Tabs 22a and 26a are seen on the upper portions of PVARP sheet 23 and MTI sheet 27, respectively. Sheets 27, 23, 18, and 22 have slots in them to accommodate rivets 16a–16e as the sheets are moved with respect to frame 17. The positions of the various sheets relative to frame 17 can be locked by a locking means comprising a threaded screw member 84 which is received by a tapped hole in knob 76. Locking is effected by tightening knob 76 against cover member 12 by rotation of knob 76 on the threaded end of screw member 84.

FIG. 4 is a back plan view of adjustable template 10 which shows a cutout portion 86 of back member 14. Base reference line 52, first transparent colored portion 58, cross hatched colored portion 62, and second transparent colored portion 64 are all printed on transparent back sheet 77 which is attached to back member 14. Since AVI sheet 18 and AEI sheet 22 have been both pulled out from frame 17, AVI fiducial line 54 and AEI fiducial line 56 are both displaced from their base position.

Referring again to FIG. 3B, an alternative embodiment of the adjustable template 10 of the present invention can be envisioned in which transparent back sheet 77 is separated from back member 14, with a space between them so that an ECG strip chart can be inserted into the space. This would have the advantage of allowing the strip chart to be kept roughly in place with respect to the frame 17 and also to be locked in place for the purpose of making a photocopy of the measurements being made.

The following are some examples of how the adjustable template 10 for pacemaker ECG analysis is used. Referring to FIG. 1C, assume that the adjustable template 10 is placed over an ECG tracing such as the one shown there. Assume that the template 10 is placed so that the zero reference line 52 coincides with the beginning of the V-pulse. The AVI sheet can then be moved left with respect to frame 17 until AVI fiducial line 54 coincides with the beginning of the A-pulse, and the AV interval can then be read by referring to the position of indicator arrow mark 68 with respect to AVI scale 30. This gives the AV interval in milliseconds. Next, AEI sheet 22 can be moved right with respect to frame 17 until AEI fiducial line 56 coincides with the beginning of the second A-pulse shown in FIG. 1C. This yields two measurements. First, the atrial escape interval in milliseconds can be read from the position of arrow indicator mark 72 with respect to AEI scale 42. Second, noting the value of AV interval already measured and referring to the position of movable AV interval scale 46 with respect to either pulses-per-minute scale 48 or pacing-interval scale 50 yields either the number of pulses per minute or the pacing interval in milliseconds, respectively. Moving PVARP sheet 23 with respect to frame 17 by means of PVARP tab 22a or PVARP tab 22b uncovers part of cross-hatched colored portion 62 to define an interval for the post ventricular atrial refractory period. Moving MTI sheet 27 with respect to frame 17 by means of MTI tab 26a or MTI tab 26b uncovers an amount of second transparent colored portion 64 which defines the maximum tracking interval.

Alternatively, the person analyzing the ECG trace sets the intervals on adjustable template 10 and then lays the template over the ECG trace. By moving the template across the ECG trace from cardiac complex to cardiac complex, the interpretation and analysis of the ECG trace is greatly simplified.

Although there have been described above specific arrangements of an adjustable template for pacemaker ECG analysis and method of use in accordance with the invention for the purpose of illustrating the manner in which the invention may be used to advantage, it will be appreciated that the invention is not limited thereto. Accordingly, any and all modifications, variations, or equivalent arrangements which may occur to those skilled in the art should be considered to be within the scope of the invention as defined in the annexed claims.

What is claimed is:

1. An adjustable template device for analyzing ECG traces, comprising:
 a frame;
 a first adjustable window means in said frame for indicating an AV interval;
 a second adjustable window means in said frame for indicating an AE interval;
 a third adjustable window means in said frame for indicating an MT interval; and
 a fourth adjustable window means in said frame for indicating a PVAR period.

2. The device of claim 1 wherein:
 said frame further comprises a base reference sheet bearing a fiducial base reference mark, an AVI scale, an AEI scale, a pulse-per-minute scale, a pacing interval scale, an MTI scale with a first transparent colored portion adjacent thereto and a PVARP scale with a second transparent colored portion adjacent thereto and a cross-hatched colored portion contiguous with said second colored portion;

said first window means comprise an AVI sheet member movable with respect to said base reference sheet, said AVI sheet member bearing first and second AV fiducial marks, an adjustable position of said first mark with respect to said base reference mark indicating a length which can be compared to a length on an ECG tracing, and an adjustable position of said second mark with respect to said AVI scale numerically indicating an AV interval;

said second window means comprise an AEI sheet member movable with respect to said base reference sheet, said AEI sheet member bearing an AEI fiducial mark and an AV interval scale, an adjustable position of said AEI mark with respect to said base reference mark indicating a length which can be compared to a length on an ECG tracing, and an adjustable position of said AV interval scale with respect to said pulses-per-minute and pacing-interval scales on said base reference sheet indicating values of pulses per minute and pacing interval, respectively, and an adjustable position of said second fiducial mark with respect to said AEI scale on said base reference sheet indicating a value for an atrial escape interval;

said third window means comprise an MTI sheet member movable with respect to said base reference sheet, said MTI sheet member bearing an MTI fiducial mark and having a first opaque portion, an adjustable position of said MTI fiducial mark with respect to said MTI scale on said base reference sheet indicating a maximum tracking interval, and an adjustable position of said first opaque portion with respect to said first transparent colored portion indicating a time interval denoted by an uncovered part of said first transparent colored portion; and said fourth window means comprise a PVARP sheet member movable with respect to said base reference sheet, said PVARP sheet bearing a PVARP fiducial mark and having a second opaque portion, an adjustable position of said PVARP fiducial mark with respect to said PVARP scale on said base reference sheet indicating a value of a post-ventricular atrial refractory period, and an adjustable position of said second opaque portion with respect to said second transparent colored portion indicating a time interval denoted by an uncovered part of said cross-hatched colored portion.

3. The device of claim 2 wherein said sheet members are comprised of plastic material.

4. The device of claim 2 wherein said frame is substantially rectangular and planar with a cover member and a back member spaced apart and connected to each other at a plurality of discrete points, said sheet members being disposed between said cover member and said back member, slidingly engaged with said frame and capable of being independently moved with respect to each other and to said frame.

5. The device of claim 4 wherein each said sheet member has at least one tab projecting therefrom outside of said frame for convenient manipulation.

6. The device of claim 5 further comprising locking means for locking said sheets in fixed positions with respect to each other and to said frame.

7. The device of claim 6 wherein said locking means comprises a screw member with a threaded portion thereof extending through said frame from said back member to said cover member and a nut member screwed onto said threaded portion adjacent said cover member, whereby a tightening of said nut member on said threaded portion of said screw member effects a locking of said positions of said sheets with respect to each other and to said frame.

8. The device of claim 2 wherein said cover member, said base reference sheet, and said movable sheet members have color coded portions associated with said marks and said scales thereon, each of said movable sheet members making use of a different color.

9. The device of claim 8 wherein said AVI, AV interval, MTI, PVARP, AEI, and pacing-interval scales are all in milliseconds.

10. The device of claim 2 further comprising a first divider sheet between said MTI sheet member and said PVARP sheet member, a second divider sheet between said PVARP sheet member and said AVI sheet member, and a third divider sheet between said AVI sheet member and said AEI sheet member, each said divider sheet being fixed in position with respect to said cover member and said back member and having cutout portions in registration with corresponding portions of said cover member revealing said AV interval scale, said MTI scale, said PVARP scale, said AEI scale, and said pulses-per-minute and pacing-interval scales.

11. The device of claim 10 wherein said cover member and said back member are fastened together with rivets, and said movable sheet members have slots therein accommodating said rivets so that said movable sheets can be slid back and forth in position with respect to said rivets and hence with respect to said cover and back members.

* * * * *